United States Patent
Fujiwara et al.

(10) Patent No.: US 12,163,123 B2
(45) Date of Patent: Dec. 10, 2024

(54) METHOD AND DEVICE FOR MANIPULATING MAGNETIC PARTICLES

(71) Applicant: SHIMADZU CORPORATION, Kyoto (JP)

(72) Inventors: Seiya Fujiwara, Kyoto (JP); Masaki Kanai, Kyoto (JP); Hiroyuki Jikuya, Kyoto (JP); Tetsuo Ohashi, Kyoto (JP); Masamitsu Shikata, Kyoto (JP); Ayaka Minamimoto, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 827 days.

(21) Appl. No.: 17/292,941

(22) PCT Filed: Nov. 22, 2018

(86) PCT No.: PCT/JP2018/043106
§ 371 (c)(1),
(2) Date: May 11, 2021

(87) PCT Pub. No.: WO2020/105159
PCT Pub. Date: May 28, 2020

(65) Prior Publication Data
US 2022/0002709 A1    Jan. 6, 2022

(51) Int. Cl.
*C12N 15/10*    (2006.01)
*B01J 19/08*    (2006.01)
(Continued)

(52) U.S. Cl.
CPC ........ *C12N 15/1013* (2013.01); *B01J 19/087* (2013.01); *B03C 1/005* (2013.01); *B03C 1/288* (2013.01)

(58) Field of Classification Search
CPC ........ B03C 1/005; B03C 1/288; B01J 19/087; C12N 15/1013
See application file for complete search history.

(56) References Cited

U.S. PATENT DOCUMENTS

| | | |
|---|---|---|
| 2013/0273552 A1 | 10/2013 | Ohashi |
| 2016/0180998 A1 | 6/2016 | Kanai et al. |
| 2017/0326509 A1* | 11/2017 | Yanagibayashi ......... C12M 1/42 |

FOREIGN PATENT DOCUMENTS

| | | |
|---|---|---|
| CN | 105709924 A | 6/2016 |
| JP | 2014-221061 A | 11/2014 |

(Continued)

OTHER PUBLICATIONS

Office Action dated Dec. 1, 2022 from the Chinese Patent Office in Application No. 201880098707.7.
(Continued)

*Primary Examiner* — Michael McCullough
*Assistant Examiner* — Kalyanavenkateshware Kumar
(74) *Attorney, Agent, or Firm* — Sughrue Mion, PLLC

(57) ABSTRACT

A purpose of the present invention is to suppress reduction in recovery rate of a target component due to a gel adhering to an inner wall surface of a treatment liquid layer. After passing magnetic particles through a gel layer, when moving the magnetic particles in the treatment liquid layer adjacent to the gel layer, the magnetic force source is automatically operated in a longitudinal direction of a tubular container so that the magnetic particles do not enter a range of a certain distance from the gel layer through which the magnetic particles have passed.

16 Claims, 3 Drawing Sheets

(51) Int. Cl.
*B03C 1/005* (2006.01)
*B03C 1/28* (2006.01)

(56) References Cited

FOREIGN PATENT DOCUMENTS

JP  2016-117032 A   6/2016
WO  2015/177934 A1  11/2015

OTHER PUBLICATIONS

Office Action dated Mar. 24, 2022 from the China National Intellectual Property Administration in CN Application No. 201880098707.7.
Office Action issued Jun. 29, 2023 in Chinese Application No. 201880098707.7.
International Search Report for PCT/JP2018/043106 dated Feb. 12, 2019 [PCT/ISA/210].
Written Opinion for PCT/JP2018/043106 dated Feb. 12, 2019 [PCT/ISA/237].

* cited by examiner

METHOD AND DEVICE FOR MANIPULATING MAGNETIC PARTICLES

CROSS REFERENCE TO RELATED APPLICATIONS

This application is a National Stage of International Application No. PCT/JP2018/043106 filed Nov. 22, 2018.

TECHNICAL FIELD

The present invention relates to a method and an apparatus for manipulating magnetic particles, for performing a process such as extraction of nucleic acid or the like using the magnetic particles.

BACKGROUND ART

It has been proposed and implemented to perform the process, such as extraction of a target component, by accommodating in a device the magnetic particles having the target component such as nucleic acid adsorbed and applying a magnetic field to the magnetic particles from an outside of the device to move the magnetic particles in the device.

A magnetic-particle-manipulator (hereinafter, also referred to as a device) for performing the above process is a device in which treatment liquid layers made of a cleaning liquid or the like and gel layers are alternately arranged in a tubular container in a longitudinal direction of the container (See Patent Document 1 and Patent Document 2).

In the magnetic-particle-manipulator, a sample layer containing the magnetic particles having the target component adsorbed is disposed at one end of the device. A magnetic force source is disposed outside the sample layer of the device to collect the magnetic particles in a sample by a magnetic field. Thus, the magnetic particles having the target component adsorbed move in the device following an operation of the magnetic force source.

The magnetic particles having the target component adsorbed can pass through the gel layer by slowly moving the magnetic force source to the other end side of the device. In a case where the treatment liquid layer is made of the cleaning liquid, when the magnetic force source is quickly reciprocated in a longitudinal direction of the device in the treatment liquid layer, the magnetic particles cannot follow the operation of the magnetic force source and are dispersed in the cleaning liquid. By this operation, contaminating components adhering to the target component are washed off in the treatment liquid layer.

After the above process is completed, the magnetic particles are moved to an eluate layer disposed at the other end of the device, and the target component is released from the magnetic particles in the eluate layer.

PRIOR ART DOCUMENTS

Patent Documents

Patent Document 1: WO2012/086243A1
Patent Document 2: WO2012/176598A1

SUMMARY OF THE INVENTION

Problems to be Solved by the Invention

When the magnetic particles pass through the gel layer, a part of gel in the gel layer often penetrates into the treatment liquid layer together with the magnetic particles and adheres to an inner wall surface of the treatment liquid layer. In that case, when the magnetic particles dispersed in the treatment liquid layer come into contact with the gel adhering to the inner wall surface, the magnetic particles are trapped in the gel, and as a result, there is a problem that recovery rate of the target component is reduced.

Therefore, an object of the present invention is to suppress reduction in the recovery rate of the target component due to the gel adhering to the inner wall surface of the treatment liquid layer.

Solutions to the Problems

There are a first method and a second method as a method according to the present invention. Both methods are methods for manipulating magnetic particles in a magnetic-particle-manipulator using a magnetic force source from an outside of the magnetic-particle-manipulator in which a treatment liquid layer and a gel layer are stacked in a tubular container in a longitudinal direction of the tubular container The first method according to the present invention is a method in which after the magnetic particles are passed through the gel layer, when the magnetic force source is automatically operated in the longitudinal direction of the tubular container in order to move the magnetic particles in the treatment liquid layer adjacent to the gel layer, an operating speed of the magnetic force source within a range of a certain distance from the gel layer through which the magnetic particles have passed is made slower than the operating speed of the magnetic force source within a range of more than the certain distance from the gel layer. By making the operating speed of the magnetic force source within the range of the certain distance from the gel layer slower than the operating speed of the magnetic force source within the range more than the certain distance from the gel layer, the magnetic particles are less likely to be trapped in the gel that can be present within the range of the certain distance from the gel layer. Thus, it is possible to reduce the magnetic particles to be trapped in the gel that has penetrated into the treatment liquid layer.

In the first method, it is preferable that the operating speed of the magnetic force source within the range of the certain distance is a speed at which the magnetic particles are not trapped in the gel present within the range of the certain distance. By doing so, it is possible to further reduce the magnetic particles to be trapped in the gel that has penetrated into the treatment liquid layer.

The second method according to the present invention is a method in which after the magnetic particles are passed through the gel layer, when the magnetic particles are moved in the treatment liquid layer adjacent to the gel layer, the magnetic force source is automatically operated in the longitudinal direction of the tubular container within a range of more than a certain distance from the gel layer through which the magnetic particles have passed. When the magnetic particles are moved in the treatment liquid layer, since the magnetic force source is operated within the range more than the certain distance from the gel layer, it is possible to prevent the magnetic particles from being trapped in the gel that can be present within the range of the certain distance from the gel layer. Thus, it is possible to reduce the magnetic particles to be trapped in the gel that has penetrated into the treatment liquid layer.

In the second method, the operating speed of the magnetic force source in a certain range closest to the gel layer in an operating range of the magnetic force source in the treatment liquid layer may be made slower than the operating speed of the magnetic force source in a range other than the certain range in the operating range. By doing so, even when the gel has penetrated into the treatment liquid layer to a position separated from the gel layer by a certain distance or more, it is possible to reduce the magnetic particles to be trapped in such gel.

There are a first apparatus and a second apparatus as apparatuses according to the present invention. Both apparatuses are apparatuses for manipulating magnetic particles in a magnetic-particle-manipulator from an outside of the magnetic-particle-manipulator in which a treatment liquid layer and a gel layer are stacked in a tubular container in a longitudinal direction of the tubular container, including: a magnetic force source that generates a magnetic force acting on the magnetic particles in the magnetic-particle-manipulator; a moving mechanism that moves the magnetic force source in the longitudinal direction of the tubular container of the magnetic-particle-manipulator; and a controller that controls an operation of the moving mechanism.

In the first apparatus according to the present invention, the controller is configured to operate the magnetic force source in the longitudinal direction of the tubular device in order to move the magnetic particles in the treatment liquid layer adjacent to the gel layer after passing the magnetic particles through the gel layer, and to make an operating speed of the magnetic force source within a range of a certain distance from the gel layer through which the magnetic particles have passed slower than the operating speed of the magnetic force source within a range of more than the certain distance from the gel layer. Since the operating speed of the magnetic force source within the range of the certain distance from the gel layer is controlled to be slower than the operating speed of the magnetic force source within the range more than the certain distance from the gel layer, the magnetic particles are less likely to be trapped in the gel that can be present within the certain distance from the gel layer. Thus, it is possible to reduce the magnetic particles to be trapped in the gel that has penetrated into the treatment liquid layer.

In the first apparatus, it is preferable that the operating speed of the magnetic force source within the range of the certain distance is a speed at which the magnetic particles are not trapped in a gel present within the range of the certain distance. By doing so, it is possible to further reduce the magnetic particles to be trapped in the gel that has penetrated into the treatment liquid layer.

In the second apparatus according to the present invention, the controller is configured to operate the magnetic force source so that the magnetic particles do not enter a range of a certain distance from the gel layer through which the magnetic particles have passed, when moving the magnetic particles in the treatment liquid layer adjacent to the gel layer after passing the magnetic particles through the gel layer. When the magnetic particles are moved in the treatment liquid layer, since the magnetic force source is controlled to operate within the range more than the certain distance from the gel layer, it is possible to prevent the magnetic particles from being trapped in the gel that can be present within the range of the certain distance from the gel layer. Thus, it is possible to reduce the magnetic particles to be trapped in the gel that has penetrated into the treatment liquid layer.

In the second apparatus, the controller may be configured to make the operating speed of the magnetic force source in a certain range closest to the gel layer in an operating range of the magnetic force source in the treatment liquid layer slower than the operating speed of the magnetic force source in a range other than the certain range in the operating range. By doing so, even when the gel has penetrated into the treatment liquid layer to a position separated from the gel layer by a certain distance or more, it is possible to reduce the magnetic particles to be trapped in such gel.

The certain distance in the method and apparatus of the present invention may be a distance equal to or more than a distance at which a gel of the gel layer has penetrated into the treatment liquid layer when the magnetic particles pass through the gel layer. The distance at which the gel penetrates into the treatment liquid layer when the magnetic particles pass through the gel layer can be determined in advance, for example, by an experiment. In this way, by moving the magnetic particles so that the magnetic particles do not enter a range of the distance at which the gel has penetrated into the treatment liquid layer from the gel layer, that is, by moving the magnetic force source within a range in which the gel is not present in the treatment liquid layer, it is possible to suppress the magnetic particles dispersed in the treatment liquid layer from being trapped in the gel adhering to the inner wall surface of the treatment liquid layer, and to prevent the reduction in the recovery rate of the target component.

An end of the gel that has penetrated into the treatment liquid layer can be optically detected from a difference in reflectance or transmittance between the treatment liquid and the gel, and the certain distance can also be obtained based on the difference. By doing so, a penetration distance of the gel into the treatment liquid layer can be accurately grasped, and it is possible to more reliably prevent the magnetic particles from being trapped in the gel that has penetrated into the treatment liquid layer.

The magnetic-particle-manipulator used in the method and apparatus of the present invention may be a device in which the treatment liquid layer and the gel layer are alternately stacked in the tubular container. Note that the present invention is not limited to such a magnetic-particle-manipulator, and may be a device including one treatment liquid layer and one gel layer.

Effects of the Invention

In the first method according to the present invention, when the magnetic particles are moved in the treatment liquid layer, since the operating speed of the magnetic force source within the range of the certain distance from the gel layer is made slower than the operating speed of the magnetic force source within the range of more than the certain distance from the gel layer, it is possible to reduce the magnetic particles to be trapped in the gel that has penetrated into the treatment liquid layer, and to suppress the reduction in the recovery rate of the target component.

In the second method according to the present invention, when the magnetic particles are moved in the treatment liquid layer, since the magnetic force source is operated within the range more than the certain distance from the gel layer, it is possible to reduce the magnetic particles to be trapped in the gel that has penetrated into the treatment liquid layer, and to suppress the reduction in the recovery rate of the target component.

In the first apparatus according to the present invention, when the magnetic particles are moved in the treatment liquid layer, since the operating speed of the magnetic force source within the range of the certain distance from the gel layer is controlled to be slower than the operating speed of the magnetic force source within the range of more than the certain distance from the gel layer, it is possible to reduce the magnetic particles to be trapped in the gel that has penetrated into the treatment liquid layer, and to suppress the reduction in the recovery rate of the target component.

In the second apparatus according to the present invention, when the magnetic particles are moved in the treatment liquid layer, since the magnetic force source is controlled to operate within the range more than the certain distance from the gel layer, it is possible to reduce the magnetic particles to be trapped in the gel that has penetrated into the treatment liquid layer, and to suppress the reduction in the recovery rate of the target component.

EMBODIMENTS OF THE INVENTION

Hereinafter, embodiments of an apparatus and a method for manipulating magnetic particles in a magnetic-particle-manipulator will be described with reference to the drawings.

Figure 1:
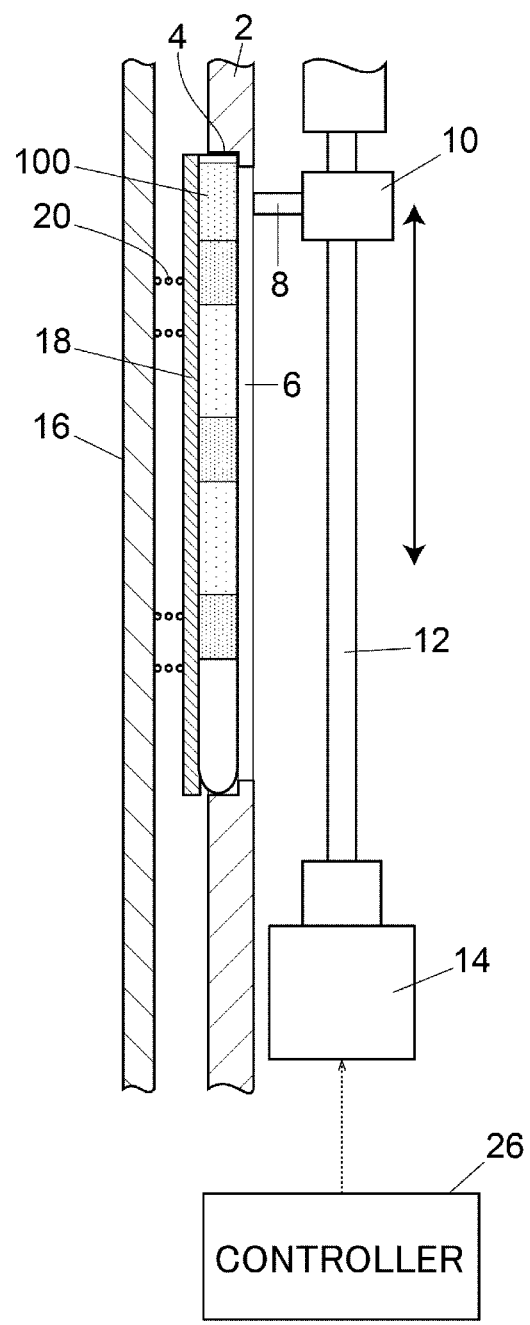
FIG. 1 is a schematic cross-sectional configuration diagram showing an embodiment of an apparatus for manipulating magnetic particles in a magnetic-particle-manipulator.

FIG. 1 schematically shows a configuration of the apparatus for manipulating the magnetic particles in a magnetic-particle-manipulator 100. The apparatus includes a front panel 2 having a recess 4 for fitting the magnetic-particle-manipulator 100 therein, and behind the front panel 2, a magnetic force source 8, a holding block 10, a ball screw 12, and a stepping motor 14.

The magnetic-particle-manipulator 100 used in this embodiment has a sample layer 102, a gel layer 108, a treatment liquid layer 104, a gel layer 108, a treatment liquid layer 104, a gel layer 108, and an eluate layer 106, that are stacked inside a tubular container in a longitudinal direction from one end side of the tubular container. Note that a device in which the treatment liquid layer 104 and the gel layer 108 are alternately stacked in this way is an example of the magnetic-particle-manipulator, and a magnetic-particle-manipulator including one treatment liquid layer 104 and one gel layer 108 is also an object of the present invention.

A sample constituting the sample layer 102 contains the magnetic particles that trap a target substance such as nucleic acid. The treatment liquid layer 104 is made of a treatment liquid for treating the target substance trapped in the magnetic particles. Examples of the treatment liquid include a cleaning liquid for removing contaminating components from the target substance trapped in the magnetic particles. An eluate constituting the eluate layer 106 is for dissolving the target substance that has been subjected to treatments such as separation and purification through the treatment liquid layer 104, and for example pure water can be used.

The magnetic force source 8 is for manipulating the magnetic particles in the magnetic-particle-manipulator 100 by applying a magnetic force to the magnetic particles from an outside of the magnetic-particle-manipulator, and is realized by, for example, a permanent magnet. The ball screw 12 is provided parallel to the longitudinal direction of the magnetic-particle-manipulator 100 fitted in the recess 4 of the front panel 2, and is rotated by the stepping motor 14. The holding block 10 is screwed with the ball screw 12, and is configured to move in an axial direction of the ball screw 12 by rotation of the ball screw 12. The holding block 10, the ball screw 12, and the stepping motor 14 constitute a moving mechanism for moving the magnetic force source 8 in the longitudinal direction of the magnetic-particle-manipulator 100.

An opening is provided in a bottom surface of the recess 4 of the front panel 2 for exposing the magnetic force source 8 to the magnetic-particle-manipulator 100 fitted in the recess 4. The magnetic force source 8 is held in the vicinity of the magnetic-particle-manipulator 100 fitted into the recess by the holding block 10, and the holding block 10 moves in the longitudinal direction of the magnetic-particle-manipulator 100 as the ball screw 12 moves in the axial direction thereof. The magnetic particles in the magnetic-particle-manipulator 100 follow an operation of the magnetic force source 8 by action of the magnetic force from the magnetic force source 8, and move in the magnetic-particle-manipulator 100 in the longitudinal direction.

An openable cover 16 that covers the front panel 2 is provided. Inside the cover 16, a pressing plate 18 for pressing the magnetic-particle-manipulator 100 fitted in the recess 4 toward the magnetic force source 8 when the cover 16 is closed is attached via an elastic member 20. When the cover 16 is closed, the pressing plate 18 comes into contact with the magnetic-particle-manipulator 100 and is urged toward the magnetic-particle-manipulator 100 by the elastic member 20, so that a warp of the magnetic-particle-manipulator 100 is corrected.

An operation of the stepping motor 14 is controlled by a controller 26. The controller 26 can be implemented by an electronic circuit including an arithmetic element and a storage medium. The controller 26 is configured to move the magnetic particles to the treatment liquid layers 104 while following the magnetic force source 8 and reciprocate the magnetic particles in the treatment liquid layers 104 in the longitudinal direction of the magnetic-particle-manipulator 100, so that the magnetic particles are moved in the treatment liquid layers 104, and to perform a predetermined treatment on the target component trapped in the magnetic particles, for example, a cleaning treatment of washing away the contaminating components.

The controller 26 slowly moves the magnetic force source 8 downward when passing the magnetic particles through the gel layer 108. At this time, as shown in FIGS. 2(A) and 2(B), the gel of the gel layer 108 often penetrated into the treatment liquid layer 104 together with the magnetic particles and adheres to an inner wall surface in the treatment liquid layer 104. If the magnetic force source 8 is operated quickly within a range in which the gel adheres to the inner wall surface of the treatment liquid layer 104, there is a possibility that the magnetic particles are trapped in the gel that has penetrated into the treatment liquid layer 104. Therefore, when the controller 26 performs the predetermined treatment on the target component in the treatment liquid layer 104, the controller 26 controls the operation of the stepping motor 14 so that the magnetic force source 8 performs an operation of making it difficult for the magnetic particles to be trapped in the gel in the treatment liquid layer 104.

Figure 2:
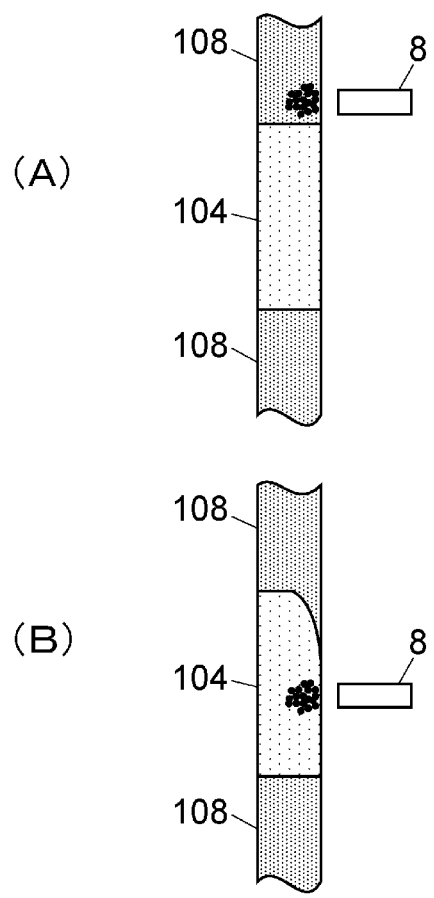
FIG. 2 is a diagram sequentially showing steps in order of moving the magnetic particles from a gel layer to a treatment liquid layer in the embodiment.
Figure 3:
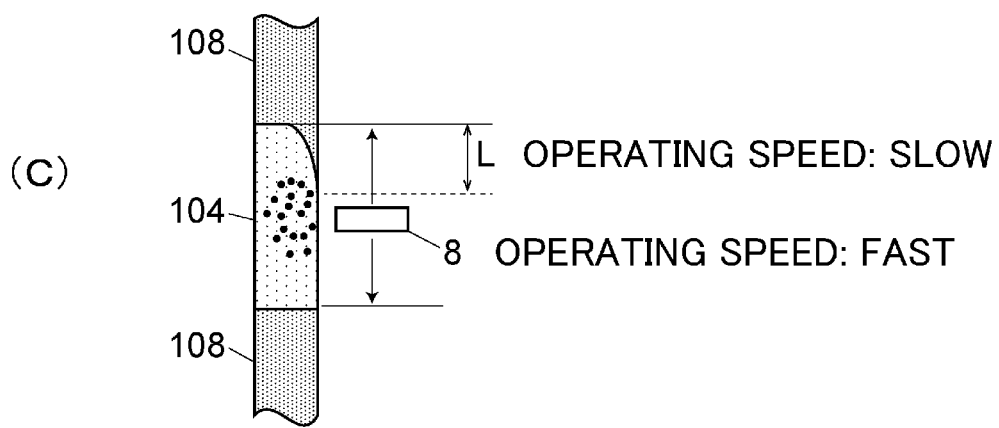
FIG. 3 is a diagram showing an example of manipulation of the magnetic particles in the treatment liquid layer.

An example of the operation of the magnetic force source 8 that makes it difficult for the magnetic particles to be trapped in the gel in the treatment liquid layer 104, is to make an operating speed of the magnetic source 8 within a range of a certain distance L from the gel layer 108 slower than that within a range of more than the certain distance L from the gel layer 108, as in FIG. 3 at (C) shown as a continuation of operations of FIG. 2 at (A) and (B). The operating speed of the magnetic force source 8 within the range of the certain distance L from the gel layer 108 is preferably a speed at which the magnetic particles are not trapped in the gel present within the constant distance L, and for example, the speed is not more than half of the operating speed within the range more than the certain distance L from the gel layer 108.

In this case, the constant distance L from the gel layer 108 may be a distance not less than a distance at which the gel can penetrate into the treatment liquid layer 104 when the magnetic particles are passed through the gel layer 108. By doing so, when the magnetic particles are moved in the treatment liquid layer 104, it is possible to reduce trapping of the magnetic particles in the gel that has penetrated into the treatment liquid layer 104, and to prevent reduction in the recovery rate of the target component.

Figure 4:
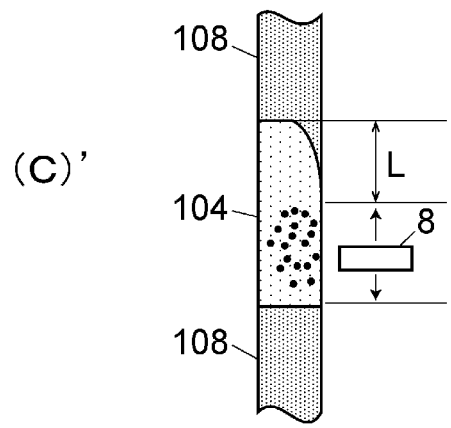
FIG. 4 is a diagram showing another example of the manipulation of the magnetic particles in the treatment liquid layer.

Another example of the operation of the magnetic force source 8 that makes it difficult for the magnetic particles to be trapped in the gel in the treatment liquid layer 104 is to operate the magnetic force source 8 only within the range more than the certain distance L from the gel layer 108, as in FIG. 4 at (C)' shown as the continuation of the operations of FIG. 2 at (A) and (B). That is, a top dead center of reciprocating motion of the magnetic force source 8 is a position farther than the certain distance L from the gel layer 108.

In this case as well, the certain distance L from the gel layer 108 may be a distance not less than the distance at which the gel can penetrate into the treatment liquid layer 104 when the magnetic particles are passed through the gel layer 108. By doing so, when the magnetic particles are moved in the treatment liquid layer 104, it is possible to reduce trapping of the magnetic particles in the gel that has penetrated into the treatment liquid layer 104, and to prevent reduction in the recovery rate of the target component.

Note that when the magnetic force source 8 is operated only within the range more than the certain distance L from the gel layer 108, the operating speed of the magnetic force source 8 in a region close to the gel layer 108 may be made slower than an operating speed in other regions. By doing so, even if by any chance the gel is present within an operating range of the magnetic force source 8, it is possible to suppress the trapping of the magnetic particles in the gel.

When the controller 26 performs the predetermined treatment on the target component in the treatment liquid layer 104, the controller 26 controls the operation of the stepping motor 14 so that the magnetic force source 8 performs an operation as shown in FIG. 3 at (C) or FIG. 4 at (C)'.

Here, a position of a boundary between each treatment liquid layer 104 and each gel layer 108 of the magnetic-particle-manipulator 100 is standardized, and the controller 26 knows in advance where is the position of the boundary between each treatment liquid layer 104 and each gel layer 108.

The distance at which the gel can penetrate into the treatment liquid layer 104 when the magnetic particles are passed through the gel layer 108 can be grasped to some extent by an experiment. Therefore, by storing in the controller 26 the distance L in consideration of a penetration distance experimentally grasped in advance, it is possible to perform the predetermined treatment without reducing the recovery rate of the target component.

Figure 5:
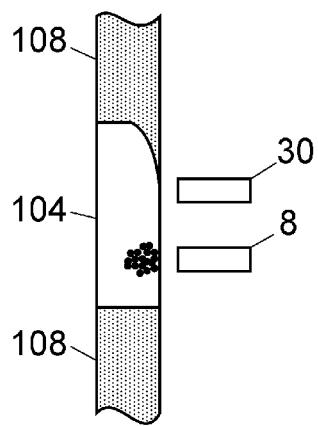
FIG. 5 is a conceptual diagram showing an embodiment of optically detecting an end of a gel that has penetrated into the treatment liquid layer.

As shown in FIG. 5, a detector 30 may be provided to optically detect an end of the gel that has penetrated into the treatment liquid layer 104 by a change in reflectance or transmittance of light. In this case, the controller 26 is preferably configured to pass the magnetic particles through the gel layer 108, and then detect a position of the end of the gel that has penetrated into the treatment liquid layer 104 by the detector 30, to determine the certain distance L from the gel layer 108 based on the position of the end of the gel. In that case, the controller 26 can be configured to cause the magnetic force source 8 to perform the operation as shown in FIG. 3 at (C) or FIG. 4 at (C)' when the controller 26 moves the magnetic particles in the treatment liquid layer 104 using the certain distance L determined by the detector 30. By doing so, it is possible to reliably reduce the trapping of the magnetic particles in the gel that has penetrated into the treatment liquid layer 104, and to prevent the reduction in the recovery rate of the target component.

DESCRIPTION OF REFERENCE SIGNS

2: Front panel
4: Recess
6: Opening
8: Magnetic force source
10: Holding block
12: Ball screw
14: Stepping motor
16: Cover
18: Pressing plate
20: Elastic member
22: Microsensor
24: Pin
26: Controller
100: Magnetic-particle-manipulator
102: Sample layer
104: Treatment liquid layer
106: Eluate layer
108: Gel layer

The invention claimed is:

1. A method for performing a process to a target component trapped by magnetic particles, wherein the method comprises:
   a preparing step of preparing a magnetic-particle-manipulator comprising a treatment liquid layer and a gel layer layered in a tubular container in a longitudinal direction of the tubular container;
   a moving step of moving the magnetic particles from the gel layer to the treatment liquid layer by manipulating the magnetic particles in the magnetic-particle-manipulator using a magnetic force source from an outside of the magnetic-particle-manipulator; and
   an operation step of automatically operating the magnetic force source in the longitudinal direction of the tubular container in order to move the magnetic particles in the treatment liquid layer after the moving step, and wherein
   in the operation step, an operating speed of the magnetic force source within a range of a certain distance from the gel layer through which the magnetic particles have passed is made slower than the operating speed of the magnetic force source within a range of more than the certain distance from the gel layer.

2. The method according to claim 1, wherein the operating speed of the magnetic force source within the range of the certain distance is a speed at which the magnetic particles are not trapped in a gel present within the range of the certain distance.

3. The method according to claim 1, wherein the certain distance is a distance equal to or more than a distance at which a gel of the gel layer has penetrated into the treatment liquid layer when the magnetic particles pass through the gel layer.

4. The method according to claim 3, wherein the certain distance is a distance obtained in advance by an experiment.

5. The method according to claim 3, wherein the certain distance is obtained by optically detecting an end of the gel that has penetrated into the treatment liquid layer.

6. The method according to claim 1, wherein the magnetic-particle-manipulator is a device in which the treatment liquid layer and the gel layer are alternately layered in the tubular container.

7. A method for performing a process to a target component trapped by magnetic particles, wherein the method comprises:
a preparing step of preparing a magnetic-particle-manipulator comprising a treatment liquid layer and a gel layer layered in a tubular container in a longitudinal direction of the tubular container;
a first moving step of moving the magnetic particles from the gel layer to the treatment liquid layer by manipulating the magnetic particles in the magnetic-particle-manipulator using a magnetic force source from an outside of the magnetic-particle-manipulator; and
a second moving step of reciprocating the magnetic force source to move the magnetic particles in the treatment liquid layer, and wherein
in the second moving step, the magnetic force source is automatically reciprocated in the longitudinal direction of the tubular container,
a top dead center of reciprocating motion of the magnetic force source in the second moving step is a position farther than a certain distance, which is a distance not less than a distance at which the gel of the gel layer can penetrate into the treatment liquid layer when the magnetic particles are passed through the gel layer directed to the treatment liquid layer, from the gel layer.

8. The method according to claim 7, wherein in the second moving step, the operating speed of the magnetic force source in a certain range closest to the gel layer in an operating range of the magnetic force source in the treatment liquid layer is made slower than the operating speed of the magnetic force source in a range other than the certain range in the operating range.

9. An apparatus for performing a process to a target component trapped by magnetic particles, wherein the apparatus comprises:
a magnetic-particle-manipulator comprising a treatment liquid layer and a gel layer layered in a tubular container in a longitudinal direction of the tubular container;
a magnetic force source that generates a magnetic force acting on the magnetic particles in the magnetic-particle-manipulator;
a moving mechanism that moves the magnetic force source in the longitudinal direction of the tubular container of the magnetic-particle-manipulator; and
a controller that controls an operation of the moving mechanism, and is configured to operate the magnetic force source in the longitudinal direction of the tubular device in order to move the magnetic particles in the treatment liquid layer adjacent to the gel layer after passing the magnetic particles through the gel layer, and to make an operating speed of the magnetic force source within a range of a certain distance from the gel layer through which the magnetic particles have passed slower than the operating speed of the magnetic force source within a range of more than the certain distance from the gel layer.

10. The apparatus according to claim 9, wherein the operating speed of the magnetic force source within the range of the certain distance is a speed at which the magnetic particles are not trapped in a gel present within the range of the certain distance.

11. The apparatus according to claim 9, wherein the certain distance is a distance equal to or more than a distance at which a gel of the gel layer has penetrated into the treatment liquid layer when the magnetic particles pass through the gel layer.

12. The apparatus according to claim 11, wherein the certain distance is preset.

13. The apparatus according to claim 9, wherein the magnetic-particle-manipulator is a device in which the treatment liquid layer and the gel layer are alternately layered in the tubular container.

14. An apparatus for performing a process to a target component trapped by magnetic particles, wherein the apparatus comprises:
a magnetic-particle-manipulator comprising a treatment liquid layer and a gel layer layered in a tubular container in a longitudinal direction of the tubular container;
a magnetic force source that generates a magnetic force acting on the magnetic particles in the magnetic-particle-manipulator;
a moving mechanism that moves the magnetic force source in the longitudinal direction of the tubular container of the magnetic-particle-manipulator; and
a controller that controls an operation of the moving mechanism, wherein
the controller is configured to move the magnetic force source to move the magnetic particles from the gel layer to the treatment liquid layer, and to reciprocate the magnetic force source to move the magnetic particles in the treatment liquid layer and
a top dead center of reciprocating motion of the magnetic force source is a position farther than a certain distance, which is a distance not less than a distance at which a gel of the gel layer can penetrate into the treatment liquid layer when the magnetic particles are passed through the gel layer directed to the treatment liquid layer, from the gel layer.

15. The apparatus according to claim 14, wherein the controller is configured to make the operating speed of the magnetic force source in a certain range closest to the gel layer in an operating range of the magnetic force source in the treatment liquid layer slower than the operating speed of the magnetic force source in a range other than the certain range in the operating range.

16. The apparatus according to claim 15, further comprising a detector that optically detects an end of the gel that has penetrated into the treatment liquid layer, wherein the controller is configured to obtain the certain distance based on a position of the end of the gel of the gel layer detected by the detector.

\* \* \* \* \*